(12) United States Patent
Tosch et al.

(10) Patent No.: US 9,285,312 B2
(45) Date of Patent: Mar. 15, 2016

(54) REFLECTION PROBE (71) Applicant: Bayer Intellectual Property GmbH, Monheim am Rhein (DE)

(72) Inventors: Stephan Tosch, Sprockhövel (DE); Reinhard Gross, Leverkusen (DE); Nils Weber, Dormagen (DE)

(73) Assignee: Bayer AG, Monheim am Rhein (DE)

( * ) Notice: Subject to any disclaimer, the term of this patent is extended or adjusted under 35 U.S.C. 154(b) by 0 days.

(21) Appl. No.: 14/374,307

(22) PCT Filed: Jan. 24, 2013

(86) PCT No.: PCT/EP2013/051326
§ 371 (c)(1),
(2) Date: Jul. 24, 2014

(87) PCT Pub. No.: WO2013/110697
PCT Pub. Date: Aug. 1, 2013

(65) Prior Publication Data
US 2014/0340683 A1    Nov. 20, 2014

(30) Foreign Application Priority Data

Jan. 25, 2012 (DE) .......... 10 2012 201 093

(51) Int. Cl.
*G01N 21/00* (2006.01)
*G01N 21/55* (2014.01)
*G01N 21/85* (2006.01)
*G01N 21/25* (2006.01)

(52) U.S. Cl.
CPC .............. *G01N 21/55* (2013.01); *G01N 21/25* (2013.01); *G01N 21/8507* (2013.01); *G01N 2201/08* (2013.01)

(58) Field of Classification Search
CPC ........ A61B 1/126; A61B 19/34; G01N 21/15; G01N 21/8507; G02B 27/0006
USPC .......... 356/301, 244, 246, 432–440
See application file for complete search history.

(56) References Cited

U.S. PATENT DOCUMENTS

| | | | | |
|---|---|---|---|---|
| 4,281,646 A * | 8/1981 | Kinoshita | ...... | 600/157 |
| 5,510,895 A * | 4/1996 | Sahagen | ...... | 356/436 |
| 5,563,737 A * | 10/1996 | Kamrat | ...... | B08B 3/02 356/128 |
| 6,873,409 B1 * | 3/2005 | Slater | ...... | 356/301 |
| 7,382,458 B2 * | 6/2008 | Johnson et al. | ...... | 356/436 |
| 7,869,028 B2 * | 1/2011 | Mannhardt et al. | ...... | 356/246 |
| 2010/0288023 A1 | 11/2010 | Leyer et al. | | |

FOREIGN PATENT DOCUMENTS

| | | |
|---|---|---|
| CA | 2862238 A1 | 8/2013 |
| DE | 202009002065 U1 | 8/2009 |
| EP | 2251682 A1 | 11/2010 |
| FR | 2372421 A1 | 6/1978 |
| WO | WO-2007098003 A2 | 8/2007 |
| WO | WO-2013/110697 A1 | 8/2013 |

OTHER PUBLICATIONS

International Search Report, PCT/EP2013/051326.
International Search Report , International Application No. PCT/EP2013/051326.

* cited by examiner

*Primary Examiner* — Hoa Pham
(74) *Attorney, Agent, or Firm* — Novak Druce Connolly Bove + Quigg LLP (57) ABSTRACT

The invention relates to a reflection probe for measuring properties of liquid and/or solid substances, and to the use thereof.

16 Claims, 3 Drawing Sheets

REFLECTION PROBE

CROSS REFERENCE TO RELATED APPLICATIONS

This application is a national stage application (under 35 U.S.C. §371) of PCT/EP2013/051326, filed Jan. 24, 2013, which claims benefit of German application no. 10 2012 201 093.9, filed Jan. 25, 2012, the entire contents of all are hereby incorporated by reference.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

STATEMENT REGARDING PRIOR DISCLOSURE BY THE INVENTOR OR A JOINT INVENTOR

Not applicable

FIELD OF THE DISCLOSURE

The invention relates to a reflection probe for measuring properties of liquid and/or solid substances, and to the use thereof.

BACKGROUND OF THE DISCLOSURE

Chemical and/or pharmaceutical processes can be controlled efficiently only if the current composition of the substance mixture and the respective properties of the individual substances of the substance mixture can be determined with sufficient accuracy in the various process steps.

The methods for the said determination of the aforementioned composition, or the aforementioned properties of the substances, include spectroscopic measurement methods.

If such spectroscopic measurement methods are used with suitable apparatuses directly in chemical and/or pharmaceutical processes, they are referred to as online spectroscopic measurement methods.

Such online spectroscopic measurement methods allow direct continuous monitoring of a running chemical and/or pharmaceutical process.

The aforementioned apparatuses suitable for online spectroscopic measurement methods include optical probes.

Online spectroscopic measurement methods are of particular importance since usually no intervention in the chemical and/or pharmaceutical process is carried out by the measurement method.

That is to say, neither the quantitative flow of the substances nor the composition of the substance mixture or the chemical nature of the substances is altered by the measurement. The latter, however, applies only when the substances of the substance mixture to be measured are chemically stable under the effect of electromagnetic radiation (usually in the form of light) which is introduced in small amounts into the process by the analysis. Yet since the amount of electromagnetic radiation required for online spectroscopic measurement methods is usually very small, this problem arises only in negligibly few cases.

Thus, if the online spectroscopic measurement method involves no intervention in the chemical and/or pharmaceutical process, the method is referred to as a noninvasive method, and here in particular a noninvasive online spectroscopic measurement method.

The aforementioned noninvasive online spectroscopic measurement methods therefore offer the combined advantages that direct sample contact of the measurement position, and therefore direct measurement value acquisition, is possible, but at the same time no sampling, preparation or other intervention needs to be carried out in the chemical and/or pharmaceutical process.

As explained above, noninvasive online spectroscopic measurement methods offer the advantage of the possibility of direct sample contact with the measurement position and therefore the possibility of direct measurement value acquisition in the running process. So that this general advantage can be fully exploited, as explained above a suitable measuring apparatus must be available.

Such suitable measuring apparatuses for noninvasive online spectroscopic measurement methods are so-called optical probes, which include the reflection probe according to the present invention.

In this context, "suitable" means in particular that the optical probe has at all times direct optical access to the substance or substance mixture to be studied.

Pharmaceutical and chemical processes are usually carried out in closed apparatuses and/or pipelines. These are generally opaque for the wavelength range which is used for the analysis.

In the said apparatuses and/or pipelines, it is therefore usually necessary to provide windows which are transparent for the wavelength range used, in order to make it possible to monitor the processes in the reactor space or the connected pipelines.

In certain applications, however, such simple windows, albeit ones which are often encountered in chemical and/or pharmaceutical processes, have significant disadvantages.

For instance, in many chemical and/or pharmaceutical processes the substances and/or substance mixtures have adhesive properties and/or are very viscous. That is to say, in running operation of the chemical and/or pharmaceutical process it happens that at least some of the substance mixtures adheres permanently on the window surface and remains there. Consequently, a noninvasive online spectroscopic measurement carried out on the window will be defective because substantially the same substance mixture, which probably does not correspond in its composition to the rest of the substance mixture which is not adhering, will constantly be analysed.

Substances and/or substance mixtures which lead to the said adhesions on such windows are in particular—to mention only two—suspensions and emulsions.

The aforementioned disadvantages give rise to the essential requirement of configuring the measuring apparatus—the probe—in such a way that operating states in which adhesions as mentioned above occur can be immediately detected, so that these can be removed and/or excluded.

In particular for use of such a measuring apparatus—probe—in pharmaceutical processes, particular requirements are to be satisfied in respect of the material quality and/or surface of the measuring apparatus, and in particular the geometry of the measuring apparatus should be configured in such a way that such adhesions either do not occur or can be fully removed from the site of the measurement.

For the input or output of electromagnetic radiation into or from the measurement position (i.e. the site for the measuring apparatus in the reactor, or in the pipeline), so called coupling lines are often used. For this reason, coupling of the electromagnetic radiation in and out is also referred to in this context.

Such coupling lines are flexible lines which make it possible to transmit electromagnetic radiation over a certain path, without accurate positioning of the optical components along this path being necessary.

Above all, glass fibre cables from the telecommunications sector are known. In connection with the measurement methods and measuring apparatuses in question here for chemical and/or pharmaceutical processes, so-called waveguide couplings or special silver halide or fluoride glass light guides are conventionally used.

The aforementioned waveguide couplings or special silver halide or fluoride glass light guides are usually suitable for the guiding of electromagnetic radiation in the mid-infrared range (400-4000 $cm^{-1}$).

In the near infrared range (NIR: 4000-14000 $cm^{-1}$) and ultraviolet/visible range (UV/Vis: 200-700 nm), it is usual to use quartz light guides which have a particularly low attenuation in these spectral ranges.

The use of such light guides is described, for example, in DE 20 2009 002065. These guide electromagnetic radiation in the form of light, emitted by a pulsed laser with an energy of 20 W per pulse, into a measuring apparatus which introduces the light into the measurement space through a sapphire glass window. The light passes through the measurement space and enters the measuring apparatus—probe—again through a further sapphire glass window, whereupon the remaining light is conveyed to an optical detector through a further light guide.

The apparatus in each configuration described in DE 20 2009 002065 is a transmission measuring apparatus. That is to say, with the aforementioned detector a measurement value is acquired which, by means of suitable calibration, makes it possible to deduce the composition of the medium present in the measurement space from the extinction of this medium. In the case of DE 20 2009 002065, the medium is milk, the fat content of which is intended to be determined.

According to DE 20 2009 002065, sapphire windows are employed because they are resistant to the abrasive media used to clean the measurement space. It follows from this that the apparatus according to DE 20 2009 002065 has the disadvantage that it cannot be operated continuously without deposits at the site of the measurement. DE 20 2009 002065 does not disclose any possibilities for keeping the site of the measurement free from, or ridding it of, deposits during running operation.

As is known, milk is an emulsion of fat in water, so that DE 20 2009 002065 reinforces in particular the existing problems of online spectroscopic measurement methods in respect of adhesions. According to the description of DE 20 2009 002065, a transmission measurement method is used because the accuracy of a reflective measurement method using a reflection probe would be insufficient. According to the indications in DE 20 2009 002065, the nature and exact origin of the reflections is not yet in fact fully understood physically.

WO 2007/098003 describes such a reflective measurement method, and a measuring apparatus—probe—suitable for such a reflective measurement method.

WO 2007/098003 also deals implicitly with the problem of a malfunction of the measuring apparatus. According to WO 2007/098003, the measuring apparatus—probe—described therein is intended, particularly under the demanding conditions of polymer extrusion, to be useable and replaceable in essential parts as well as recalibratable, without the polymer extrusion process having to be stopped therefor.

According to WO 2007/098003, this problem is resolved in that a unit comprising an optical window is connected firmly by a screw-in device to the apparatus/pipeline in which measurement is to be carried out, the optical window in turn being closed in a leaktight fashion relative to the measurement space by means of a further screw-in device. As a consequence of this, the further measuring arrangement located behind the unit comprising the optical window can be replaced without requiring an intervention in the method.

However, the measuring apparatus according to WO 2007/098003 also does not prevent polymer from adhering to the optical window, or provide devices which could remove such polymer without interrupting the polymer extrusion process.

A feature common to the two measuring apparatuses—probes—described above for noninvasive online spectroscopic measurement is thus the fact that they do not comprise devices which make it possible to keep the site of the measurement free from adhesions without interrupting the chemical and/or pharmaceutical process in question. Therefore, none of the aforementioned measuring apparatuses—probes—can represent continuously correct measurement operation for noninvasive online spectroscopic measurement without interruption of the chemical and/or pharmaceutical process in question.

From the prior art, it is therefore likewise known that besides the measuring apparatus—probe—a suitable cleaning device is applied which makes it possible to clean the measurement position even during operation of the chemical and/or pharmaceutical process, without the latter having to be interrupted therefor. However, this is to be installed in addition to the noninvasive online spectroscopic measuring apparatus, and per se constitutes a further site at which adhesions may form.

As an alternative, measuring apparatuses—probes—of the general type are also known which already have such a cleaning device integrated. Such measuring apparatuses—probes—known from the prior art are, however, usually constructed in such a way that they are installed beside the measurement position in an enlarged holding device, as described for instance in WO 2007/098003.

In the prior art, however, such measuring apparatuses—probes—with an integrated cleaning device are configured in such a way that the cleaning device is raised relative to the measurement position, in order to send a directional flushing jet onto the measurement position.

The effect of this is that they cannot be used in existing equipment comprising moving devices, in particular scraping the inner wall, since in this way at least the cleaning device would come in contact because of the moving parts, such as blades or stirrers. In the least problematic case, this leads to the cleaning device being damaged; in the worst case, the cleaning device blocks the moving parts.

For use in pharmaceutical production, such designs prove to be uncleanable, or poorly cleanable, if only because of the aforementioned raised nature and the further edges and recesses resulting therefrom, and are often not integratable into such processes.

BRIEF SUMMARY OF THE DISCLOSURE

On the basis of the described prior art, it is therefore an object to provide a measuring apparatus—probe—which permits noninvasive online spectroscopic measurement of properties of liquid and/or solid substances in chemical and/or pharmaceutical processes while having a compact design and comprising a cleaning device, without thereby entailing the above problems of the prior art. In particular, the device is intended to allow continuous operation of the chemical and/or pharmaceutical process without defective measurements occurring because of adhesions at the site of the measurement.

The instant disclosure therefore relates to a measuring apparatus in the form of a reflection probe, comprising a measurement position in the form of a window in a window surface and a cleaning device in the form of a flushing nozzle in a front surface, characterized in that the window is integrated in a planar fashion into the window surface, which is inclined at an angle of from 10° to 25° relative to the front surface of the measuring apparatus, the flushing nozzle being integrated into the front surface which is reduced by the proportion of the window surface, and the outlet opening of the flushing nozzle being located adjacent to the window surface in the front surface. The disclosure also relates to methods of using the measurement apparatus.

DETAILED DESCRIPTION OF THE DISCLOSURE

The aforementioned object is achieved according to the invention by a measuring apparatus in the form of a reflection probe (1), comprising a measurement position in the form of a window (4) in a window surface (3) and a cleaning device in the form of a flushing nozzle in a front surface (2), characterized in that the window (4) is integrated in a planar fashion into the window surface (3), which is inclined at an angle of from 10° to 25° relative to the front surface (2) of the measuring apparatus, the flushing nozzle being integrated into the front surface (2) which is reduced by the proportion of the window surface (3), and the outlet opening (5) of the flushing nozzle being located adjacent to the window surface (3) in the front surface (2).

By virtue of the aforementioned arrangement of the window, window surface, flushing nozzle and its outlet opening, a body is obtained which has two plane surfaces, of which one plane surface—the window surface—has a small setting angle but is otherwise free of corners and edges which could generate adhesions.

The second plane surface—the front surface reduced by the proportion of the window surface—comprises the outlet opening of the flushing nozzle as a further geometrical discontinuity at the edge of the window surface, although this is automatically kept free from adhesions by the flushing.

Overall, an apparatus is obtained which on the one hand makes it possible to keep the window, and therefore the site of the measurement, free from adhesions without the overall apparatus having a multiplicity of geometrical discontinuities, which could promote adhesions.

Together with the small setting angle, the overall apparatus can be integrated into the wall of the apparatus/pipeline while being almost planar therewith. Any adhesions possibly formed behind the obliquely set window surface are therefore minimized in scope and moreover do not influence the measurement values acquisition.

The setting angle is preferably from 12° to 20°, particularly preferably from 14° to 18°, especially preferably 15°, 16° or 17°.

The small setting angle of the window surface relative to the front surface is advantageous because in this way the fluid emerging from the flushing nozzle never arrives parallel to the window surface, so that the flushing effect of the fluid is ensured even when the medium of the chemical/pharmaceutical process is very viscous and/or tacky, and a thin boundary layer would otherwise be formed on the window surface.

If in such a case the window surface were flowed onto parallel or at an angle of less than 10°, as indicated according to the invention, it would not be possible to ensure that this boundary layer is also flushed away.

On the other hand, the maximum setting angle of 25° relative to the front surface means, on the one hand, that the flushing fluid does not rebound at elevated pressure and therefore only cleans parts of the window surface—rather, the entire site of the measurement is flushed and jointly cleaned—and on the other hand it means that in this way the overall apparatus only deviates to a small extent from a planar front surface, so that installation of the apparatus into existing equipment which comprises moving parts, in particular devices scraping the inner wall, is made possible and the further possibility of the formation of adhesions is also minimized.

The above-mentioned preferred setting angles reinforce the positive effect just mentioned.

As described above, a window is integrated in a planar fashion into the window surface. During use of the measuring apparatus according to the invention, the window is in contact with the process space of the chemical and/or pharmaceutical process.

According to the invention, a window is intended to mean a component of the measuring apparatus which is at least partially transparent for electromagnetic radiation. Preferably, the window is at least partially transparent for electromagnetic radiation in the wavelength range of from 200 to 700 nm (UV/Vis) and/or in the wave number range of from 400 to 4000 $cm^{-1}$ (IR) and/or from 4000 to 14000 $cm^{-1}$ (NIR).

Partial transmission is intended to mean at least 50% transmission, that is to say at least 50% of the incident radiation passes through the window.

The integration of the window into the window surface may be carried out by generally known means. These include adhesive bonding, screwing and/or clamping of the window into an excision from the window surface. Thus, according to the invention, the window surface has an excision into which the window is integrated in a planar fashion with the window surface.

Preferably, the aforementioned excision is configured in such a way that, on the side in the direction of the space in which the chemical/pharmaceutical process is carried out (the process space), the window surface has an opening which has an area larger than the area of the opening of the excision on the opposite side, the window having the shape and area of the opening in the direction of the process space.

This embodiment is particularly advantageous because in this way the window has an increased cross-sectional area compared with the area of the opening on the opposite side from the process space, so that the window is prevented from slipping through the window surface. Furthermore a seal from the surroundings is established by the window either through the pressure of the intrinsic weight of the window or through the pressure of the process in the process space against the resulting side-edge surface of the process space. In particular, this means that, in the case of processes which are operated at high elevated pressure and which therefore have increased requirements for pressure-tightness, a self-reinforcing sealing effect is thereby achieved since, with an increasing pressure in the process space, the application pressure of the window against the side-edge surface also increases, and the sealing effect is therefore simultaneously increased.

The cross-sectional shape of the window in the window surface may be selected in any desired way; for example, the window may be configured circularly, squarely or polygonally in its cross section, so long as it is ensured that the window is integrated in a planar fashion into the window surface.

Since the window surface has a setting angle relative to the front surface, however, it is preferred for the window to be a body which has the same setting angle relative to the front surface on the side of the window surface as the window surface but is parallel to the front surface on the opposite side.

In the case of a circular window, this would produce a cylinder which is chamfered on the side of the window surface.

This embodiment is particularly preferred in conjunction with the aforementioned preferred embodiment of the opening in the window surface for receiving the window, because in this way the pressure acting against the window (for example also generated by the flushing fluid flowing against the window) is converted into a force which only acts orthogonally against the aforementioned side-edge, which further reinforces any sealing effect.

The opening geometry of the flushing nozzle is also to a large extent selectable in any desired way. It has, however, been found that a flushing nozzle outlet geometry which has an extent parallel to the front surface at least equal to the extent of the window perpendicularly to the outlet opening is to be preferred. The effect achieved by this is that the entire window in the window surface is flushed over by the flushing fluid and can therefore be kept free of adhesions.

Configuration of the outlet opening of the flushing nozzle in the form of a slot or slit on the edge formed by contact of the front surface with the window surface is preferred in particular, this slot or slit in particular being configured to be at least as wide as, and particularly preferably precisely as wide to 10% wider than, the extent of the window perpendicularly to the outlet opening, the ratio of the width of the slot or slit to its height being at least 5. Particularly preferably, the ratio is at least 10. In particular preferably at least 10 but at most 15.

The effect achieved by this is that the flushing fluid leaves the outlet opening of the flushing nozzle in a rectangular channel flow which is at least as wide as the extent of the window perpendicularly to the outlet opening. The flushing fluid therefore reliably flows over the window surface over its entire width, which improves the cleaning effect. The aforementioned ratios mean an outlet opening of the nozzle narrowing increasingly heightwise, and therefore an increase in the formation of turbulent shedding edges of the flow at the outlet opening of the flushing nozzle. A turbulent channel flow thereby produced over the window further improves the cleaning effect.

The outlet opening of the flushing nozzle of the present measuring apparatus according to the invention is usually supplied with a flushing fluid via an associated bore and/or a corresponding supply line.

Particularly in the case of the aforementioned preferred outlet opening in the form of a slot/slit, it is in this case preferred for the supply line and/or bore for supplying the flushing nozzle to be offset relative to the outlet opening of the flushing nozzle along an extended line between the window and the flushing nozzle. An offset by at least 1.1 times the maximum dimension (diameter in the case of bores) of the supply line is particularly advantageous.

This has the advantage that a full flow profile can be formed in the flushing nozzle, or in the section between the flushing nozzle inlet and the outlet opening, which in turn reinforces the aforementioned advantages.

If the flushing nozzle is not intended to be operated continuously, then it is preferred for a nonreturn valve to be provided in the apparatus, for example between the flushing nozzle and the supply line, or merely in the supply line, in order to prevent process medium from emerging when no flushing fluid is applied.

The measuring apparatus according to the invention may be introduced into a case.

If the measuring apparatus has a significant extent orthogonally to the front surface, then the measuring apparatus itself forms such a case. Otherwise, the measuring apparatus is usually screwed or clamped into the case.

The case of the measuring apparatus is then introduced into the wall of the apparatus/pipeline into which the measuring apparatus is intended to be integrated. The introduction of the case (or measuring apparatus) into the wall of the apparatus/pipeline is usually also carried out by screwing or clamping it in. Particularly when the measuring apparatus does not itself form the case, introduction of the case into the wall by permanent connection, for example welding, is preferred.

The measuring apparatus according to the invention usually also comprises an outer sealing means, which seals the measuring apparatus against the process space at the case, or when the measuring apparatus itself forms the case it seals the measuring apparatus against the wall of the apparatus/pipeline.

A sealing means is intended to mean a means known to the person skilled in the art for pressure-tight sealing, for example O-ring seals, adhesive bonds or soldered connections.

If the measuring apparatus is not a component of the case, then this case is used to frame the components of the measuring apparatus when these form separate components. That is to say the case would then frame the window surface and the front surface.

Either by means of the aforementioned case or—when the measuring apparatus itself forms the case—in the measuring apparatus, according to the invention the side of the window facing away from the process space makes contact with a so-called probe shaft.

In this context, a probe shaft means at least one above-described coupling line for the guiding of electromagnetic radiation, particularly in the form of light, for instance the said light guides, these however being framed in an essentially rigid shaft. Such a shaft is usually constructed cylindrically, and comprises at least one light guide.

If only one light guide is used, then a filter, which separates the electromagnetic radiation coupled in via the one light guide from that which is intended to be coupled out, is connected to the light guide. Such a filter may, for example, be implemented by at least partial thermal fusion of at least two light guides.

Preferably, the probe shaft comprises at least two light guides, of which at least one is used to couple electromagnetic radiation into the measuring apparatus and at least one other is used to couple out and feed back the radiation to be measured. In this case, the light guides for coupling out radiation are spatially separated from those for coupling in, so that the diffuse radiation possibly occurring in the edge region of the light guides cannot lead to crosstalk of the signals between the two light guide types. The spatial separation may, for example, be implemented by two separate bores in the probe shaft, through which the light guides respectively intended for coupling in and coupling out are fed.

The number of light guides used for coupling in need not be the same as the number of light guides used for coupling out. Preferably, more light guides are provided in the probe shaft for coupling the radiation out than light guides for coupling the radiation in, since the amount of electromagnetic radiation to be coupled out is at most as great as that which was coupled in. Usually, however, the amount of radiation to be coupled out is significantly less than that which was coupled in. For a high yield of radiation coupled out and a resultingly sufficiently intense signal, it is therefore advantageous to provide a greater number of light guides for coupling the electromagnetic radiation out.

The comments above apply with the assumption of the same optical cross section of the light guides in the probe shaft. If the optical cross sections of the light guides in the probe shaft are not the same, then the comments made above relating to the number apply similarly for the sum of all the optical cross sections of the light guides for coupling electromagnetic radiation in in relation to the sum of all the optical cross sections of the light guides for coupling electromagnetic radiation out. That is to say, in total a greater optical cross section of the light guides for coupling out is preferably provided in the probe shaft compared with the optical cross section for coupling in.

In connection with the present invention, a ratio of the optical cross section of the light guides coupling in to that of the light guides coupling out of between four and six to one has been found to be particularly advantageous. That is to say for each proportion of cross section of the light guides coupling out, from four to six times as much cross section of the light guides coupling in is available.

For the aforementioned contacting of the probe shaft with the window, the case, or if the measuring apparatus itself forms the case, the case/measuring apparatus, has a recess (a bore in the case of a cylindrical probe shaft) for receiving the probe shaft, which corresponds in diameter to the outer diameter of the probe shaft.

The case, or the measuring apparatus when the measuring apparatus itself forms the case, furthermore has a further recess (a further bore in the case of a cylindrical recess), which corresponds to the aforementioned supply line for the flushing fluid.

Particularly preferably, the measuring apparatus itself forms the case and has two bores, of which one is the supply line for the flushing fluid to the flushing nozzle and its outlet opening, and the other is the bore for receiving the probe shaft.

It is preferable that the probe shaft can be removed from the bore (7) for receiving the probe shaft, for example for better cleaning or repair, and reinserted into the bore (7) for receiving the probe shaft, in which case the optical properties should be re-established precisely, particularly when using a light guide bundle. Furthermore, the light guides should bear flush on the window (9).

Known spring-loaded systems for the probe shaft (for example Reflector Flush from the company Solvias, http://www.solvias.com/sites/default/files/reflector-flush-english_final.pdf) do not have rotation protection, so that the orientation is lost during reinsertion. Furthermore, they comprise structures which are not flush with the window and which constitute an adhesion point for contamination.

In a preferred embodiment of the apparatus, the probe shaft is mounted securely against rotation in the bore (7) for receiving the probe shaft, by means of a spring-loaded connector with rotation protection.

In the measuring apparatus according to the invention, a plug with an orientation guide, in particular a spring-loaded connector locked with rotation protection, is preferably used during the insertion into the bore (7), which simultaneously has the following properties:

establishing the orientation after removal and reinsertion into the bore (7) for receiving the probe shaft in the same way, and pressing the probe shaft, which preferably contains at least one light guide, into the bore (7) for receiving the probe shaft by means of a spring force, so that the light guides directly bear flush on the window.

As a special plug, a bayonet connector with rotation protection is used in particular, for instance an ST plug/BFOC plug, or a spring-loaded screw connector with rotation protection.

If the probe shaft comprises a light guide bundle of light guides, the use of a spring-loaded connector with rotation protection is particularly advantageous because the bundle would have different optical properties when it is pressed in with a different orientation in the bore (7) for receiving the probe shaft.

The advantage for the user is therefore that, by using a spring-loaded connector with rotation protection, the same optical properties of the probes can also be re-established after removal and reinsertion of the probe shaft. This is particularly important because the window located in front of the light guide (in the inserted state) is not planar but is inclined at an angle.

Such a measuring apparatus is usually configured cylindrically. This measuring apparatus then preferably has a diameter of from 12 to 18 mm. In such designs, and in the case of measuring apparatuses as described above with a slit and/or slot of the outlet opening, it is preferred for the slit/slot to have a height of from 0.5 to 1 mm. That is to say, the width of such a slit or slot is preferably at least 2.5 to 5 mm, particularly from 5 to 10 mm, more particularly preferably from 5 to 10 mm, but at most from 7.5 mm to 15 mm.

The measuring apparatus—probe—according to the invention is particularly suitable for the optical monitoring of solid processes, one- or multiphase liquid processes, and liquid processes in the presence of solids, for instance suspensions, in which the possibility of contamination of the window surface during the running process exists.

Monitoring is intended to mean tracking as a function of time one or more process parameters of the chemical and/or pharmaceutical process which can provide information about the progress of the process. Such process parameters are in particular the properties of liquid and/or solid substances which are treated in the chemical and/or pharmaceutical process. These include, for instance, concentration and temperature.

The monitoring involves the acquisition of one or more parameters and evaluation of the measured parameter values. The evaluation may, for example, consist in comparison of a measured parameter value with a setpoint value or regulation of the manipulated process variables on the basis of one or more parameter values.

The preferably process-integrated tracking of quality features and process parameters is used for monitoring correct operation, early detection of irregular states and processes, and associated limitation of the effects of perturbations.

The continuous process monitoring thereby made possible may therefore be used as a warning system, in order to avoid expensive process interruptions and plant shutdowns. The setpoint/actual value comparison in real time, which is possible with process-integrated monitoring, may also be used in order to deliberately influence processes by changing manipulated variables (process regulation).

Optical monitoring is intended to mean that the interaction of a substance present in the process with electromagnetic radiation is used in order to acquire a process parameter. For example, the concentration of a substance in a process may be tracked by measuring the absorption and/or reflection of incident electromagnetic radiation.

The measuring apparatus—probe—according to the invention is suitable in particular for monitoring processes in which the susceptibility of the probe to contamination, or the retention of product residues, needs to be minimized. Product residues mean remainders from previous production cycles remaining on the probe. Particularly in pharmaceutical and/or food technology processes, such product residues may detrimentally affect the running process and the quality of the product produced.

Product residues remaining on the window may also vitiate the parameter value measured. The probe according to the invention makes it possible to monitor such processes by ensuring, on the basis of its geometry and by purging with gas or a cleaning agent, that the window surface of the probe is free of product residues before the start of an individual measurement.

The present invention therefore also relates in particular to the use of the measuring apparatus according to the invention in pharmaceutical and food technology methods for the spectroscopic monitoring thereof.

Here, the measuring apparatus according to the invention proves to be particularly advantageous because on the one hand it continuously has no deposits at the site of the measurement and, furthermore, is configured geometrically in such a way that almost no deposits are also formed on and around the measuring apparatus due to flow stagnations or geometrical discontinuities.

The present invention furthermore relates to the use of the measuring apparatus according to the invention in paddle dryers and granulators.

Here, the measuring apparatus according to the invention proves to be particularly advantageous because, owing to its low elevation, it does not interfere with these apparatuses in their operation and is also not itself damaged thereby. The aforementioned paddle dryers and granulators are furthermore apparatuses in which at least partial modification of the phase states of the substances being treated occurs in the scope of the process carried out in these apparatuses. For instance, suspensions or wet solids are often treated in such apparatuses, so that the processes carried out are solid processes in the presence of liquids. Particularly in such processes, the formation of adhesions is particularly likely, which allows the advantages of the measuring apparatus according to the invention to stand out more.

The present invention will now be explained with reference to the figures, but without being restricted thereto.

Figure 1:
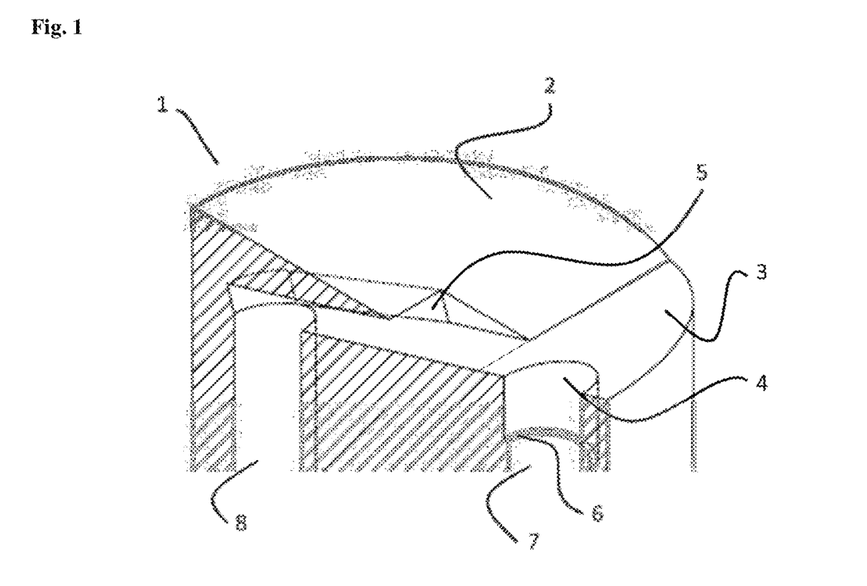
FIG. 1 shows a schematic representation of a measuring apparatus of the instant disclosure.

FIG. 1 shows a schematic representation of a preferred embodiment of the measuring apparatus (1) according to the invention, comprising a front surface (2) and a window surface (3), which is set at an angle of 17° relative to the front surface. The window surface (3) comprises an opening (4) for a window, the opening having a side-edge (6) in the direction of the bore (7) for the probe shaft (not represented). On the edge on which the window surface and front surface meet, an outlet opening (5) of a flushing nozzle is formed, which is supplied with the flushing fluid via a bore (8) offset relative to the outlet opening. The represented embodiment of the measuring apparatus itself forms the case, so that the latter is not represented.

Figure 2:
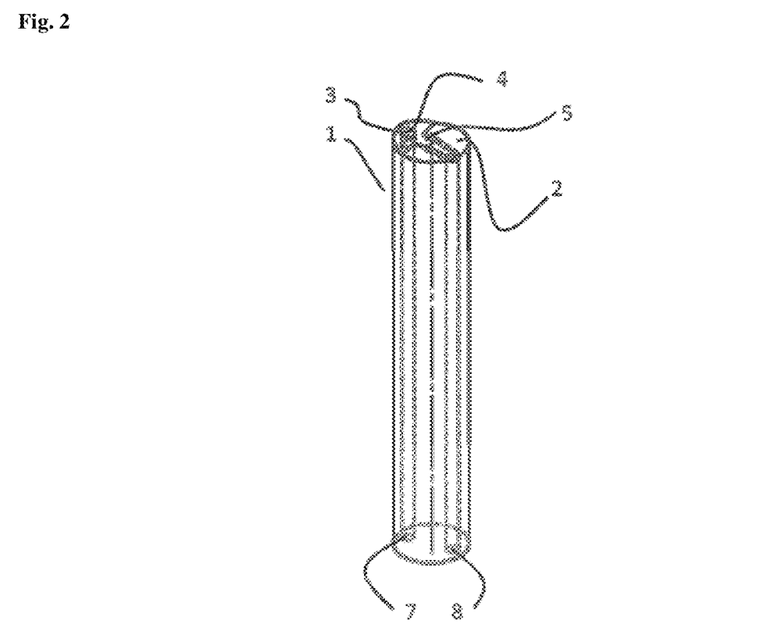
FIG. 2 shows an overall view of the measuring apparatus represented in FIG. 1.

FIG. 2 shows an overall view of the measuring apparatus represented in FIG. 1, which itself forms the case.

Figure 3:
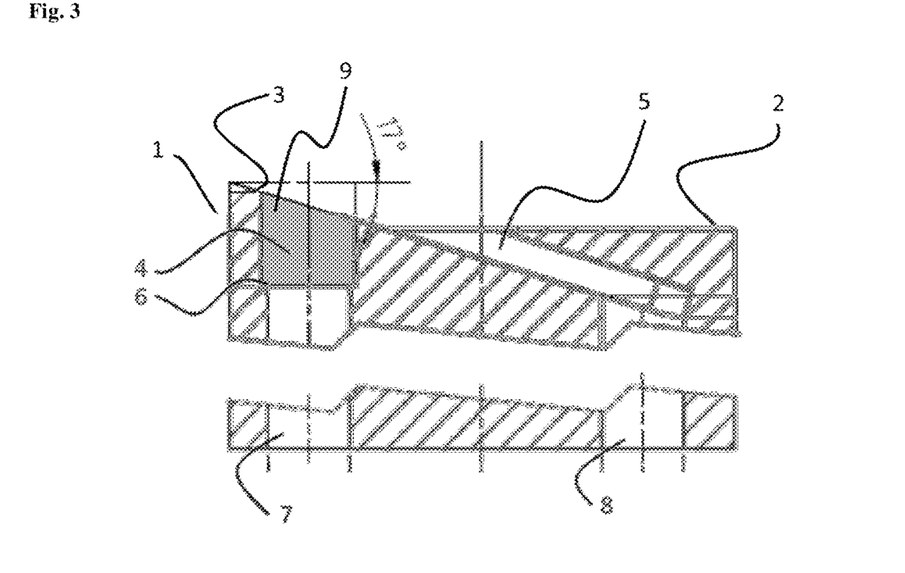
FIG. 3 shows a sectional representation of the three-dimensional representation of the measuring apparatus of FIG. 1.

FIG. 3 shows a sectional representation of the three-dimensional representation of the measuring apparatus as represented in FIG. 1, together with the window (9) in the opening (4), which is configured cylindrically and is chamfered on the window surface, so that it forms a plane surface therewith.

Figure 4:
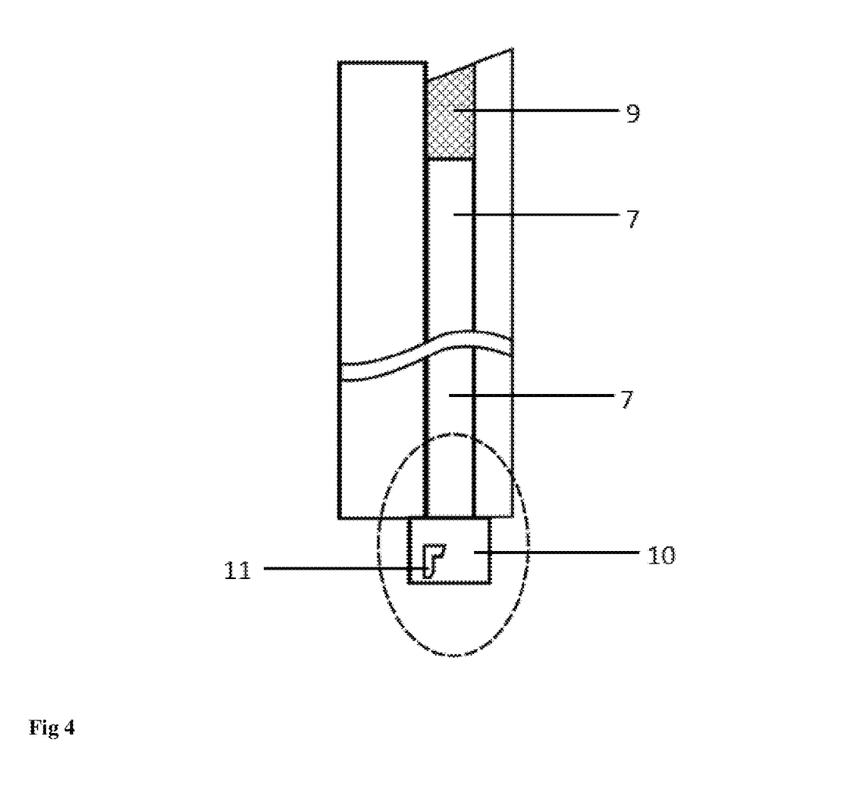
FIG. 4 shows a sectional representation of the bore of the measuring apparatus.

FIG. 4 shows a sectional representation of the bore (7) for receiving the probe shaft, the insert comprising a bayonet connector (10) with rotation protection (11).

Figure 5:
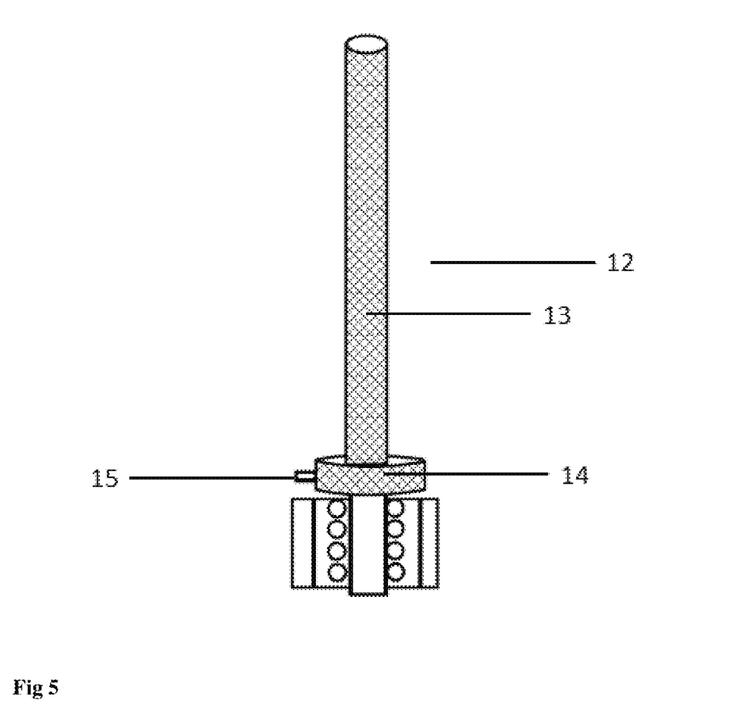
FIG. 5 shows a sectional representation of the probe shaft the measuring apparatus.

FIG. 5 shows a sectional representation of a probe shaft (12), the probe shaft comprising a light guide bundle (13) with an insert (14), the insert (14) having a lock (15) complementary with the bayonet connector (10) with rotation protection (11) of the measuring apparatus of FIG. 4.

The invention claimed is:

1. Measuring apparatus in the form of a reflection probe, comprising a measurement position in the form of a window in a window surface and a cleaning device in the form of a flushing nozzle in a front surface, characterized in that the window is integrated in a planar fashion into the window surface, which is inclined at an angle of from 10° to 25° relative to the front surface of the measuring apparatus, the flushing nozzle being integrated into the front surface which is reduced by the proportion of the window surface, and the outlet opening of the flushing nozzle being located adjacent to the window surface in the front surface.

2. Measuring apparatus according to claim 1, characterized in that the opening for the window is configured as an excision that has an opening in the direction of the process space, which has an area larger than the area of the opening of the excision on the opposite side, the window having the shape and area of the opening in the direction of the process space.

3. Measuring apparatus according to claim 2, characterized in that the window is a body which on the side of the window surface has the same setting angle relative to the front surface as the window surface but is parallel to the front surface on the opposite side.

4. Measuring apparatus according to claim 2, characterized in that the outlet opening of the flushing nozzle has an extent parallel to the front surface at least equal to the extent of the window perpendicularly to the outlet opening.

5. Measuring apparatus according to claim 2, characterized in that the flushing nozzle is supplied with a flushing fluid via a supply line, and the supply line is offset relative to the outlet opening of the flushing nozzle along an extended line between the window and the flushing nozzle.

6. Measuring apparatus according to claim 2, characterized in that it has a case comprising a bore for receiving a probe shaft, in which bore the probe shaft is screwed or clamped.

7. Measuring apparatus according to claim 1, characterized in that the window is a body which on the side of the window surface has the same setting angle relative to the front surface as the window surface but is parallel to the front surface on the opposite side.

8. Measuring apparatus according to claim 7, characterized in that the outlet opening of the flushing nozzle is configured in the form of a slot or slit on the edge formed by contact of the front surface with the window surface.

9. Measuring apparatus according to claim 1, characterized in that the outlet opening of the flushing nozzle is configured in the form of a slot or slit on the edge formed by contact of the front surface with the window surface.

10. Measuring apparatus according to claim 9, characterized in that the ratio of the width of the slot or slit to its height is at least 5.

11. Measuring apparatus according to claim 1, characterized in that the outlet opening of the flushing nozzle has an extent parallel to the front surface at least equal to the extent of the window perpendicularly to the outlet opening.

12. Measuring apparatus according to claim 1, characterized in that the flushing nozzle is supplied with a flushing fluid via a supply line, and the supply line is offset relative to the outlet opening of the flushing nozzle along an extended line between the window and the flushing nozzle.

13. Measuring apparatus according to claim 1, characterized in that it has a case comprising a bore for receiving a probe shaft, in which bore the probe shaft is screwed or clamped.

14. Measuring apparatus according to claim 13, characterized in that the probe shaft is mounted securely against rotation in the bore in order to receive the probe shaft by means of a spring-loaded connector with protection against rotation.

15. A method of using the measuring apparatus according to claim 1, comprising the step of incorporating the measuring apparatus in pharmaceutical and food technology processes for the spectroscopic monitoring thereof.

16. A method of using the measuring apparatus according to claim 1 comprising the step of placing or affixing the measuring apparatus at a location where the measuring apparatus can monitor the contents of a paddle dryer or a granulator.

* * * * *